大wert(12) United States Patent
Sutherland et al.

(10) Patent No.: US 9,261,444 B1
(45) Date of Patent: Feb. 16, 2016

(54) APPARATUS, SYSTEM, AND METHOD FOR IN SITU STRENGTH TESTING OF A BONDED JOINT

(71) Applicant: The Boeing Company, Chicago, IL (US)

(72) Inventors: Richard M. Sutherland, Port Orchard, WA (US); Eugene A. Dan-Jumbo, Bothell, WA (US)

(73) Assignee: The Boeing Company, Chicago, IL (US)

( * ) Notice: Subject to any disclaimer, the term of this patent is extended or adjusted under 35 U.S.C. 154(b) by 261 days.

(21) Appl. No.: 13/954,732

(22) Filed: Jul. 30, 2013

(51) Int. Cl.
*G01N 17/00* (2006.01)
*G01N 3/02* (2006.01)
*G01N 3/08* (2006.01)
*G01N 3/30* (2006.01)
*G01N 3/307* (2006.01)
*G01N 19/04* (2006.01)
*G01N 19/00* (2006.01)
*G01L 5/00* (2006.01)
*G01N 29/04* (2006.01)
*G01N 1/22* (2006.01)
*G01N 3/00* (2006.01)

(52) U.S. Cl.
CPC .. *G01N 3/02* (2013.01); *G01N 3/08* (2013.01); *G01N 3/30* (2013.01); *G01N 3/307* (2013.01); *G01L 5/008* (2013.01); *G01N 1/2208* (2013.01); *G01N 3/00* (2013.01); *G01N 19/00* (2013.01); *G01N 19/04* (2013.01); *G01N 29/045* (2013.01); *G01N 2203/0246* (2013.01); *G01N 2203/0296* (2013.01); *G01N 2203/0676* (2013.01)

(58) Field of Classification Search
CPC ........... G01N 3/30; G01N 3/08; G01N 3/307; G01N 3/00; G01N 19/04; G01N 19/00; G01N 29/045; G01N 2203/0246; G01N 2203/0296; G01N 2203/0676; G01N 1/2208; G01M 7/08; G01M 17/00; G01L 1/00; G01L 5/008
USPC ............ 73/12.01, 12.09, 12.05, 12.04, 12.11, 73/12.13, 150 A, 150 R
See application file for complete search history.

(56) References Cited

U.S. PATENT DOCUMENTS

| | | | | |
|---|---|---|---|---|
| 3,605,486 A * | 9/1971 | Goodman et al. | ............... | 73/788 |
| 4,530,246 A * | 7/1985 | Pitman et al. | .................. | 73/799 |
| 5,841,034 A * | 11/1998 | Ball | ............................... | 73/800 |
| 7,398,698 B2 * | 7/2008 | Griess et al. | .................... | 73/801 |
| 7,669,467 B2 * | 3/2010 | Breuer et al. | ............... | 73/150 A |
| 8,250,928 B2 * | 8/2012 | Miller et al. | .................... | 73/779 |
| 8,616,068 B2 * | 12/2013 | Miller et al. | .................... | 73/779 |
| 2002/0190729 A1 * | 12/2002 | Wilson | ......................... | 324/663 |
| 2010/0162825 A1 * | 7/2010 | Karp et al. | ..................... | 73/799 |

* cited by examiner

*Primary Examiner* — Lisa Caputo
*Assistant Examiner* — Jonathan Dunlap
(74) *Attorney, Agent, or Firm* — Kunzler Law Group, PC

(57) ABSTRACT

The present disclosure relates to a system for testing the strength of a bonded joint between at least two components, wherein the system includes at least one element force energizer that creates an actual mechanical stress in the bonded joint when actuated, wherein the element force energizer is coupled with the at least two components. The system further includes an energy interface that is connectable to a power source, the energy interface being in electrical communication with the at least one element force energizer, and a sensor that detects the actual mechanical stress or strain in the bonded joint. The system may also include a recording device that records and/or transmits the detected mechanical stress or strain in the bonded joint. In one example, the element force energizers include piezoelectric materials.

16 Claims, 6 Drawing Sheets

APPARATUS, SYSTEM, AND METHOD FOR IN SITU STRENGTH TESTING OF A BONDED JOINT

FIELD

This disclosure relates to testing the strength of a bonded joint and more particularly relates to a system, apparatus, and method for in situ testing of bonded joints using element force energizers and sensors.

BACKGROUND

Connecting various components together is a step in many manufacturing processes and numerous systems and methods exist for joining multiple components together. The term "joint" refers to the point or location between at least two components coupled together. For example, multiple elements may be coupled together at a joint through the use of fasteners (e.g., screws, bolts, nails, straps, etc), interlocking pieces, welding techniques, and/or adhesive compositions. Each of these methods for joining components together has its advantages and disadvantages depending on various factors (such as the size, weight, and composition of the components and the humidity, temperature, and pressure of the environment), and each type of coupling has a corresponding strength rating. The strength of a coupling is ascertained by testing the joined components to determine if the joint is sufficiently strong to withstand required load thresholds and if the joint has the durability to hold up over a useful lifecycle. These joint tests, and the corresponding strength ratings, can be important for the safety of users that operate, exploit, interact with, or otherwise use end-products with joints and coupled components.

Generally, the procedures and systems for testing joints involve controllably increasing a load on a joint or subjecting the joint to repeated load cycles, and determining if the joint can sustain the proof load, if defects occur, and/or if the joint reaches a failure point. For example, joints can be tested to determine the load range in which the joint is elastic (i.e., the range in which the joint does not suffer any permanent damage or distortion), the load range in which the joint is plastic (i.e., the range in which the joint still is capable of sustaining a load but permanent damage and distortion has occurred, resulting in permanent defects), and the load range in which the joint fails.

Conventional strength tests are generally performed ex situ and usually include applying shear, compression, and/or tensile type forces to the joint. For example, when conventionally testing an adhesive coupling ("bonded joint"), as may be found in a frame of an aircraft, the joint is often removed from its position in the frame (i.e., the frame is disassembled to a certain degree) or a similar joint is tested instead of the actual joint. Continuing the example of bonded joints in aircrafts, many governmental airline agencies, such as the Federal Aviation Agency (FAA) in the United States, require periodic maintenance checks to ensure the safe operation of all the aircrafts within their jurisdictions. For example, 'C-checks' and 'D-checks' are maintenance checks that are required by the FAA every few years on airplanes in the United States and such checks often require joint testing and joint inspection. Because conventional joint testing systems and methods are performed ex situ, these checks often involve substantial cost and expense as the testers have to disassemble large portions of the aircraft. In other words, conventional testing systems and procedures are not well suited for testing the strength of joints in situ. Additionally, conventional testing systems also involve visually detecting cracks, defects, or other visible evidences of failure.

SUMMARY

The subject matter of the present disclosure has been developed in response to the present state of the art, and in particular, in response to the limitations of conventional joint testing systems. Specifically, conventional joint testing methods and systems do not allow for joints to be tested in situ. Accordingly, the subject matter of the present disclosure has been developed to provide an apparatus, system, and method for strength testing bonded joints in situ that overcome at least some of the above-discussed shortcomings of the prior art.

The present disclosure relates to a system for testing the strength of a bonded joint between at least two components, wherein the system includes at least one element force energizer that creates an actual mechanical stress in the bonded joint when actuated, wherein the element force energizer is coupled with the at least two components. The system further includes an energy interface that is connectable to a power source, the energy interface being in electrical, hydraulic, or some other form of energy transmission communication with the at least one element force energizer, and a sensor that detects the actual mechanical stress in the bonded joint. The system may also include a recording device that records and/or transmits the detected mechanical stress in the bonded joint. In one example, the element force energizers include piezoelectric materials.

According to one embodiment, the element force energizers may create mechanical stress according to a predetermined mechanical fatigue profile. The element force energizers may also be embedded in the at least two components or embedded in a patch that spans the bonded joint. Also, the element force energizers and the sensors may include load cells or piezoelectric materials.

The present disclosure also relates to a controller apparatus for testing the strength of a bonded joint between at least two components, wherein the controller includes a stress simulator module configured to generate a predetermined mechanical fatigue profile, wherein the predetermined mechanical fatigue profile comprises desired mechanical stress commands. The controller also includes an element force energizer module configured to receive the mechanical fatigue profile and control element force energizers coupled to the at least two components to create an actual mechanical stress in the bonded joint according to the mechanical fatigue profile. Still further, the controller includes a sensor module configured to detect the actual mechanical stress in the bonded joint.

The controller may further include a recorder module that receives and records the actual mechanical stress/strain detected by the sensor module. Also, the element force energizers may be integrated into the at least two components or integrated into a patch that spans the bonded joint. The element force energizers may also include piezoelectric materials or load cells.

The present disclosure also relates to a method for testing the strength of a bonded joint between at least two components. The method includes supplying power to an energy interface coupled to element force energizers, controlling the element force energizers to create an actual mechanical stress/strain in the bonded joint based on the power, and measuring the actual mechanical stress/strain in the bonded joint. The method may further include recording the actual mechanical stress/strain measured in the bonded joint or embedding the element force energizers into the at least two components proximate the bonded joint.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

As described above, there are different methods for coupling two or more elements together. The present disclosure relates to permanently bonding components together with an adhesive composition ("bonded joint") and further relates to testing the strength of bonded joints between at least two components. There are many mechanical structures that use bonded joints for permanently coupling components together. For example, in the aerospace industry bonded joints may be implemented throughout the frame, substructure, and exterior paneling of an aircraft to hold various elements together. In these applications, the bonded joints must withstand harsh temperatures, pressures, humidity ranges, weather conditions, and other environmental situations. Additionally, the bonded joints must withstand the repeated and substantial load involved with daily flying. In other examples, bonded joints can be implemented in the manufacturing and/or repair of composite-bodied automobiles, commercial aircraft, military aircraft, and spacecraft, among others.

Figure 1A:
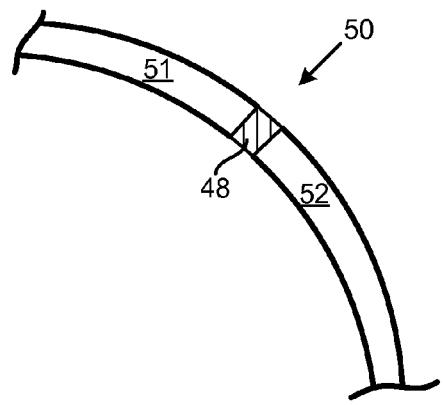
FIG. 1A depicts one embodiment of a bonded joint between two components.

FIG. 1A depicts one embodiment of a bonded joint 50 between two components 51, 52 that are held together using an adhesive 48. As described above, the two components 51, 52 may be elements of any structure, such as a frame of an aircraft or a component in a motor vehicle. While in the depicted embodiment the components 51, 52 are curved or arcuate, it is contemplated that the components 51, 52 may be straight or may have other configurations. The type of bonded joint 50 depicted in FIG. 1A is a butt joint that couples the two components 51, 52 together at their tips or ends. Other examples of different types of bonded joints are described below.

There are many different types of adhesives that can be used in bonded joint applications, according to the specifics of a given implementation. In one embodiment, an adhesive is selected for its ability to bond with certain materials. In another embodiment, the adhesive is selected for its ability to withstand various environmental conditions. For example, bonding two polymer composites 51, 52 together may require an epoxy or a urethane adhesive. In another embodiment, in which two metal materials are being bonded together, a methacrylate adhesive may be used. In other words, the components 51, 52 may be made from metallic, composite, or ceramic materials. It is contemplated that other types of adhesives, such as epoxy adhesives, polyamide adhesives, bismaleimide adhesives, and thermoplastic adhesives, among others, may be used in the bonded joints of the present disclosure.

Figure 1B:
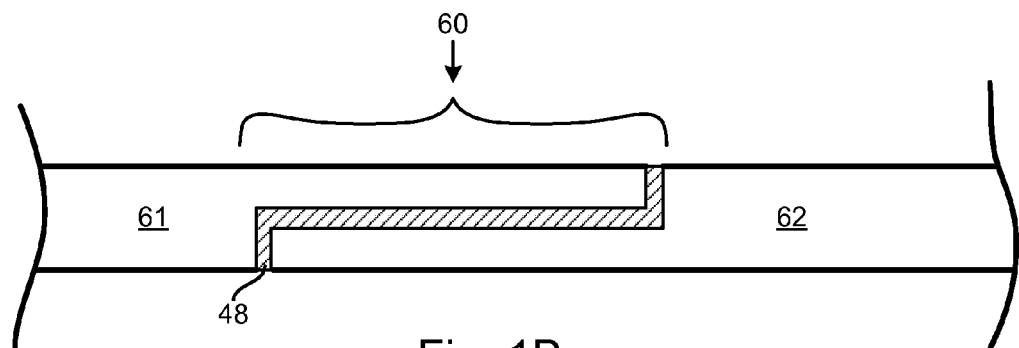
FIG. 1B depicts another embodiment of a bonded joint between two components.

FIG. 1B depicts another embodiment of a bonded joint 60 between two components 61, 62. In the depicted embodiment, the bonded joint 60 is a stepped-lap joint in which the two components 61, 62 have complementary step configurations that allow for an adhesive 48 to bond the two components together along multiple planes. In other words, the stepped-lap joint 60 may be stronger than a simple butt joint 50 because the components 61, 62 have both vertical and horizontal bonding surfaces, and the bonded joint 60 is strengthened by the overlapping nature of the two components 61, 62. It is contemplated that other configurations may be employed for bonding multiple components together. For example, basic lap joints, tapered-lap joints, scarf joints, and strap joints (see FIG. 1C), among others.

Figure 1C:
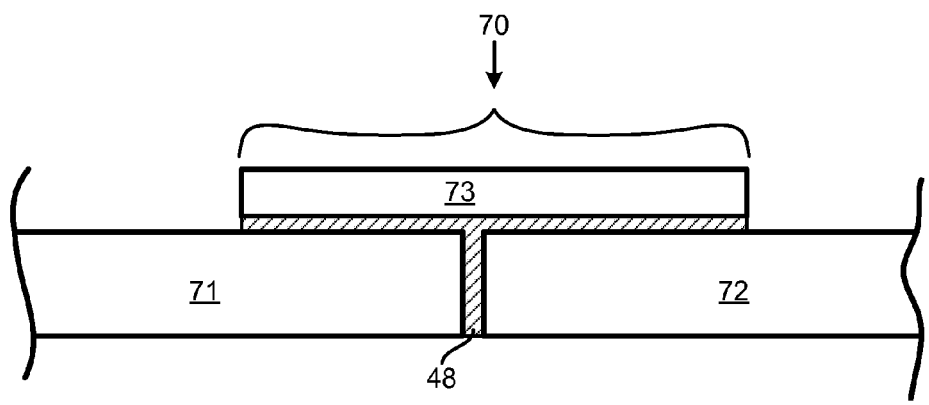
FIG. 1C depicts one embodiment of a bonded joint between three components.

FIG. 1C depicts another embodiment of a bonded joint 70 between three components 71, 72, 73. The top component 73 is sometimes referred to as a strap or a patch. This top component 73 spans across the bonded regions of the two other components 71, 72 and provides improved strength and stability. The material of the components 71, 72, 73 may be the same or different depending on the specifics of given implementation and the characteristics of the particular application in which the joint is used. Additionally, multiple adhesives 48 may be used, either mixed together to form a hybrid adhesive or applied separately to different components. For example, a first type of adhesive may be applied to bond two metal components together (e.g., 71, 72) and a second type of adhesive may be applied to bond a composite component (e.g., 73) to the metal components (e.g., 71, 72).

Figure 2:
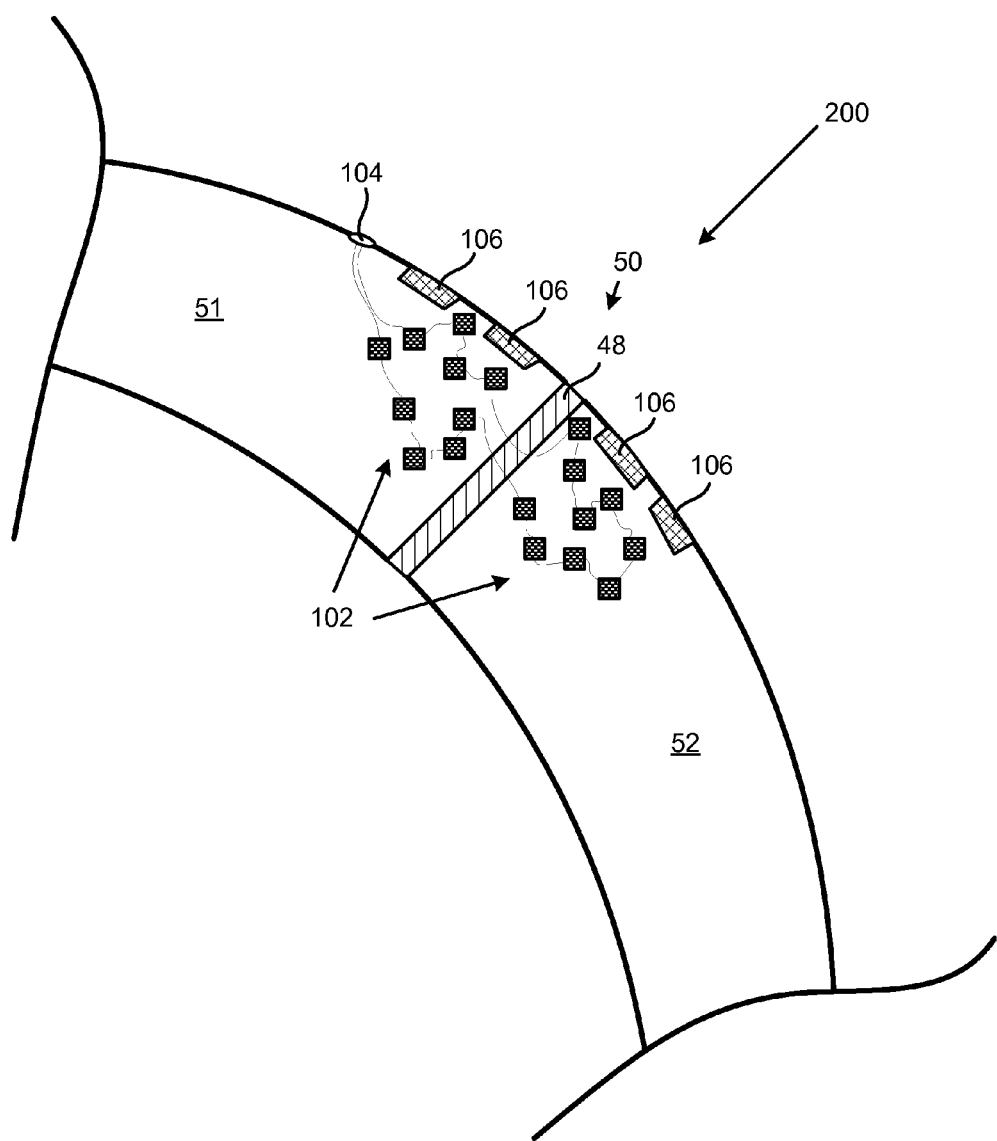
FIG. 2 depicts one embodiment of a system for in situ strength testing of a bonded joint that includes element force energizers, an energy interface, and a sensor.

FIG. 2 depicts one embodiment of a system 200 for in situ strength testing of a bonded joint 50 that includes element force energizers 102, an energy interface 104, and sensors 106. As described above, conventional strength testing systems and methods are generally performed ex situ. In other words, the bonded joint components have to be tested before they are installed/assembled in the final product or the final product has to be disassembled to remove the bonded joint components for periodic maintenance testing. In the system depicted in FIG. 2, however, bonded joint components can be tested in situ (i.e., in place, in their assembled or installed positions). This is achieved, according to one embodiment, by coupling element force energizers 102 to the components 51, 52 of the bonded joint 50. In one embodiment, the element force energizers 102 apply a load to the bonded joint 50 in order to simulate the stress and strain that the bonded joint 50 will experience during actual use. In other words, the load actually applied to the joint 50 by the element force energizers 102 represents a typical use of the bonded joint—e.g., an aircraft in flight. According to one embodiment, the element force energizers may be force actuators. Sensors 106 are used to measure and detect the mechanical stress and strain caused by the element force energizers 102. In some implementations, the element force energizers 102 and/or the sensors 106 are integrated with or embedded into the components 51, 52. According to some implementations, the element force energizers 102 and/or the sensors 106 are integrated with or embedded into a patch that is bonded across the joint 50 (see, e.g., FIGS. 3 and 4 for additional details regarding the patch).

In the depicted embodiment, the element force energizers 102 are integrated with or embedded into the components 51, 52. The element force energizers 102 are configured to simulate a load or a cycle of loads by exerting a force on the components 51, 52. Depending on the orientation and configuration of the element force energizers 102, the force exerted on the components 51, 52 may be shear, compression, or tensile type forces. The element force energizers 102 may include piezoelectric materials that are actuated with an electrical current or pressure elements actuated by a working fluid. Piezoelectric materials are certain solid materials (e.g., various types of crystals, ceramics, proteins, etc.) that accumulate an electric charge when deformed. The inverse is also true of piezoelectric materials in that such materials also change their dimensions when an electric field is applied to the material. Thus, piezoelectric materials are well suited to function as element force energizers 102 in the disclosed system 200 because they can change their size depending on the strength of the electrical, thereby causing the surround components 51, 52 and bonded joint 50 to experience mechanical stress and strain. It is contemplated that other actuators or elements that are capable of creating mechanical stress, force, or strain in a material fall within the scope of this disclosure and that such other actuators would be recognized by those of ordinary skill in the art in view of this disclosure.

Additionally, although the element force energizers 102 are depicted in the Figures as having a specific shape and a specific size in relation to the other components, the shape, dimensions, quantity, configuration, and relative sizes of the various components in the Figures are not intended to limit the scope of the present disclosure. In other words, in one implementation the element force energizers 102 may be so small that they might be hardly visible to the naked eye. Therefore, for purposes of clarifying the disclosure, the element force energizers 102 are depicted throughout the Figures as having a certain size, shape, position, and quantity, and thus are only illustrative of one embodiment of the general structural configuration of an in situ strength testing system for a bonded joint.

The energy interface 104 includes electrical connections or electrical ports to which a power supply may be attached. The energy interface 104 allows the system 200 to be electrically connected to a voltage source in order to power the element force energizers 102. The energy interface 104, according to one embodiment, may include a covering or a cap that can be opened or removed during testing and closed or attached again after the strength testing has concluded. Therefore, the cap may protect the exposed electrical wiring and may function to preserve the aesthetic or aerodynamic features of the structure (e.g., the exterior paneling of an airplane wing). In one embodiment, the energy interface 104 may include tape or other temporary adhesive that covers and protects the wiring. According to one embodiment, the system 200 may also include a controller device, either upstream or downstream from the energy interface 104, that controls the power flowing into the element force energizers 102. For example, the electricity flowing into the system 200 may be regulated so that the element force energizers 102 produce a controlled stress/strain on the bonded joint 50 and the components 51, 52. Thereby the intensity and magnitude of the force imparted to the components 51, 52 and the joint may be regulated.

In another embodiment, the element force energizers 102 may be configured to actuate according to a mechanical fatigue profile that represents and simulates a typical load/stress lifecycle of the bonded joint 50. For example, the mechanical fatigue profile for a bonded joint structure in an aircraft may include multiple high intensity force actuations that simulate repeated take-offs and landings and/or repeated periods of mild force actuations that simulate in-flight turbulence and other in-flight conditions.

FIG. 2 also depicts sensors 106 that detect the stress in the bonded joint 50 and/or the components 51, 52 as a result of the element force energizers 102. As defined herein, detecting or measuring the stress in a bonded joint may include detecting or measuring the strain in the bonded joint, and calculating the stress in the bonded joint based on the detected or measured strain in the bonded joint. Therefore, the terms stress and strain can be used interchangeably according to this defined relationship. According to one embodiment, the sensors 106 may include multiple sensors positioned along the length of the joint 50 and the components 51, 52. In another embodiment, the sensors 106 may include a single panel sensor that covers portions of the bonded joint 50 and the components 51, 52. The sensors 106 may be integrated with and embedded into the components 51, 52 or the sensors 106 may be integrated with and embedded into a patch that is bonded across the joint 50 (see, e.g., FIGS. 3 and 4 for additional details regarding the patch). It is also contemplated that the sensors 106 may be removable and thus may be indirectly and selectively coupled to the components 51, 52 during periods of testing. Additional details relating to the various contemplated configurations are included below with reference to FIG. 3.

The sensors 106 may be piezoelectric materials. As briefly described above, piezoelectric materials are capable of accumulating an electric charge when such materials are subject to forces that deform or otherwise change the dimensions of a material. The power of the accumulated (measured) electric charge is directly proportional to the magnitude of the change in dimension, thus piezoelectric materials are able to detect minute changes, strains, and deformations in the bonded joint 50 and components 51, 52, thereby allowing the system 200 to measure and report an actual strength rating for a specific bonded joint 50.

According to one embodiment, the sensors 106 may be transducer load cells. Transducer load cells convert force into an electrical signal. The mechanism by which load cells convert force into an electrical signal involves two stages. First, the force created by the element force energizers 102 strains a wire to the extent that the resistance of the wire is altered. Based on the altered resistance of the strained wire in the load cells, the sensor 106 is then able to calculate, through the use of look-up tables or algorithms, the magnitude of the force that strained the wire. It is contemplated that other sensors 106 capable of detecting and/or measuring stress, force, or strain in a material fall within the scope of this disclosure, and that such sensors would be recognizable by those of ordinary skill in the art in view of this disclosure.

The sensors 106 may also be fiber optic sensors in some embodiments.

Additionally, although the sensors 106 are depicted in the Figures as having a specific shape and a specific size in relation to the other components, the shape, dimensions, quantity, configuration, and relative sizes of the various components in the Figures is not intended to limit the scope of the present disclosure. In other words, in one implementation the sensors 106 may be so small that they might be hardly visible to the naked eye. Therefore, for purposes of clarifying the disclosure, the sensors 106 are depicted throughout the figures as having a certain size, shape, position, and quantity, in order to show one embodiment of the general structural configuration of an in situ strength testing system for a bonded joint.

Figure 3:
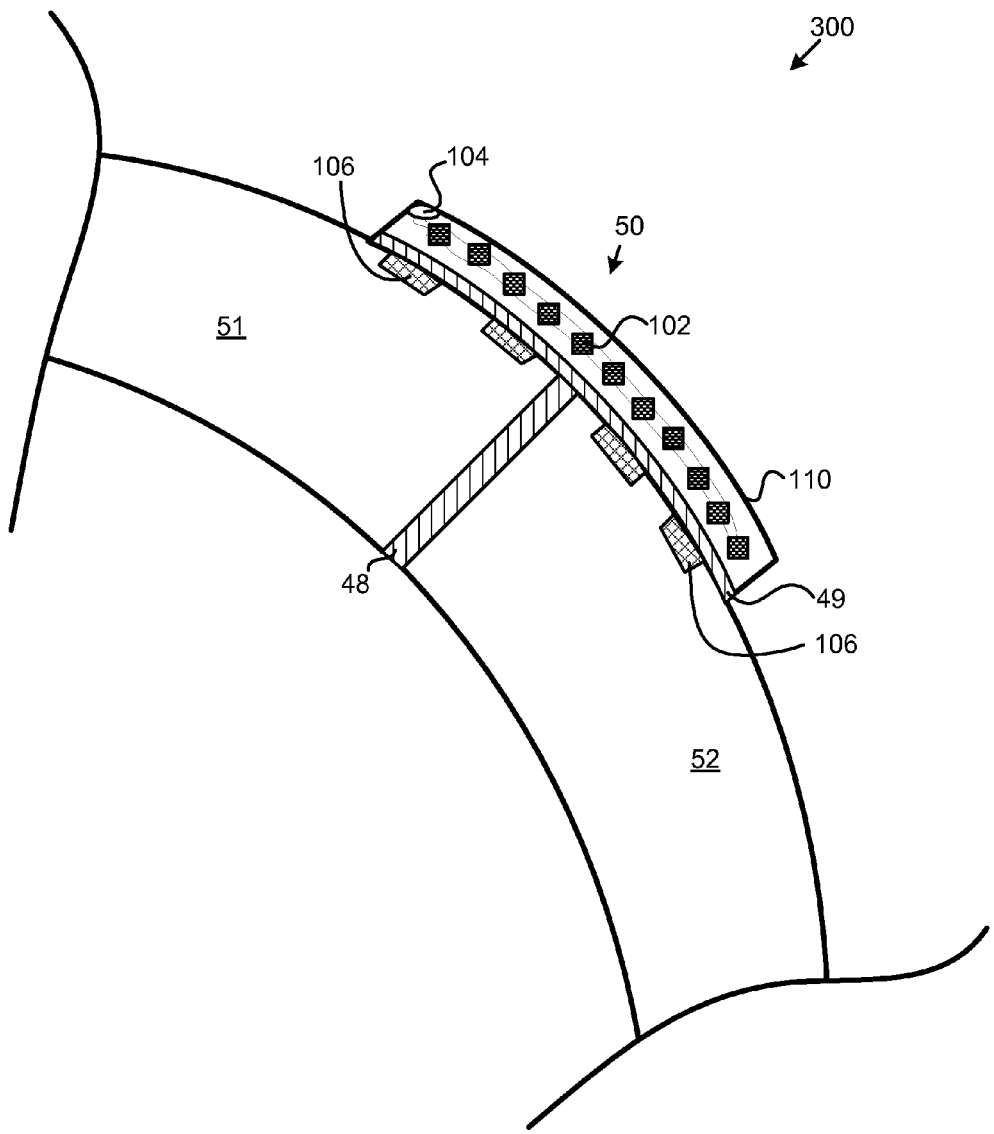
FIG. 3 depicts another embodiment of a system for in situ strength testing of a bonded joint that includes element force energizers, an energy interface, and a sensor.

FIG. 3 depicts another embodiment of a system 300 for in situ strength testing of a bonded joint 50 that includes element force energizers 102, an energy interface 104, a sensor 106, and a patch 110. As described briefly above, in some implementations the bonded joint 50 may include a patch or strap 110 that extends over the two bonded components 51, 52. The patch 110 may be constructed of the same material as the other components 51, 52 or the patch may comprise a different material. According to the depicted embodiment, the patch 110 may have the element force energizers 102 embedded therein and may also have the energy interface 104 attached thereto. Further, the sensors 106 may also be embedded in the patch 110 or the sensors 106 may be embedded in the components 51, 52. During a testing procedure, the element force energizers 102 and the sensors 106 are in contact with the components 51, 52 and/or the joint 50. The contact may be direct, as seen in FIG. 2 where the actuators 102 and the sensors 106 are embedded into and integrated with the components 51, 52, or indirect, as depicted in FIG. 3 where the actuators 102 are embedded in the patch 110 and are thus indirectly coupled to the components 51, 52 via the patch.

In one embodiment, the patch 110 may be permanently bonded across the joint 50 via an adhesive 49 (the patch may actually be considered an element of the bonded joint 50) and in another embodiment the patch 110 may be configured to be removable or detachable. In other words, the patch 110 may be permanently bonded to the components 51, 52 so that during regular operation of the structure (e.g., flying an aircraft with a bonded joint in the airframe) the patch 110 remains in place. In other implementations the patch may only be attached to the bonded joint 50 when the system 300 is testing the strength of the joint, such as, for example, during periodic maintenance checks, and then removed when the testing procedure is over. In the temporary embodiment, the patch may be temporarily attached with fasteners or otherwise coupled to the components 51, 52 and/or bonded joint 50 during testing.

According to one embodiment, the system of the present disclosure may be used as a manufacturing system that checks the installed or assembled final product. In another embodiment, the system of the present disclosure may be implemented and used periodically throughout the useful life of the product to check the strength of the bonded joints (e.g., as briefly described above regarding the airplane c-checks and d-checks). In yet another embodiment, it is contemplated that the system may be implemented as a retro-fit package to be installed on an existing structure or as an integral element in the structure of a product during its initial fabrication or manufacture.

Figure 4:
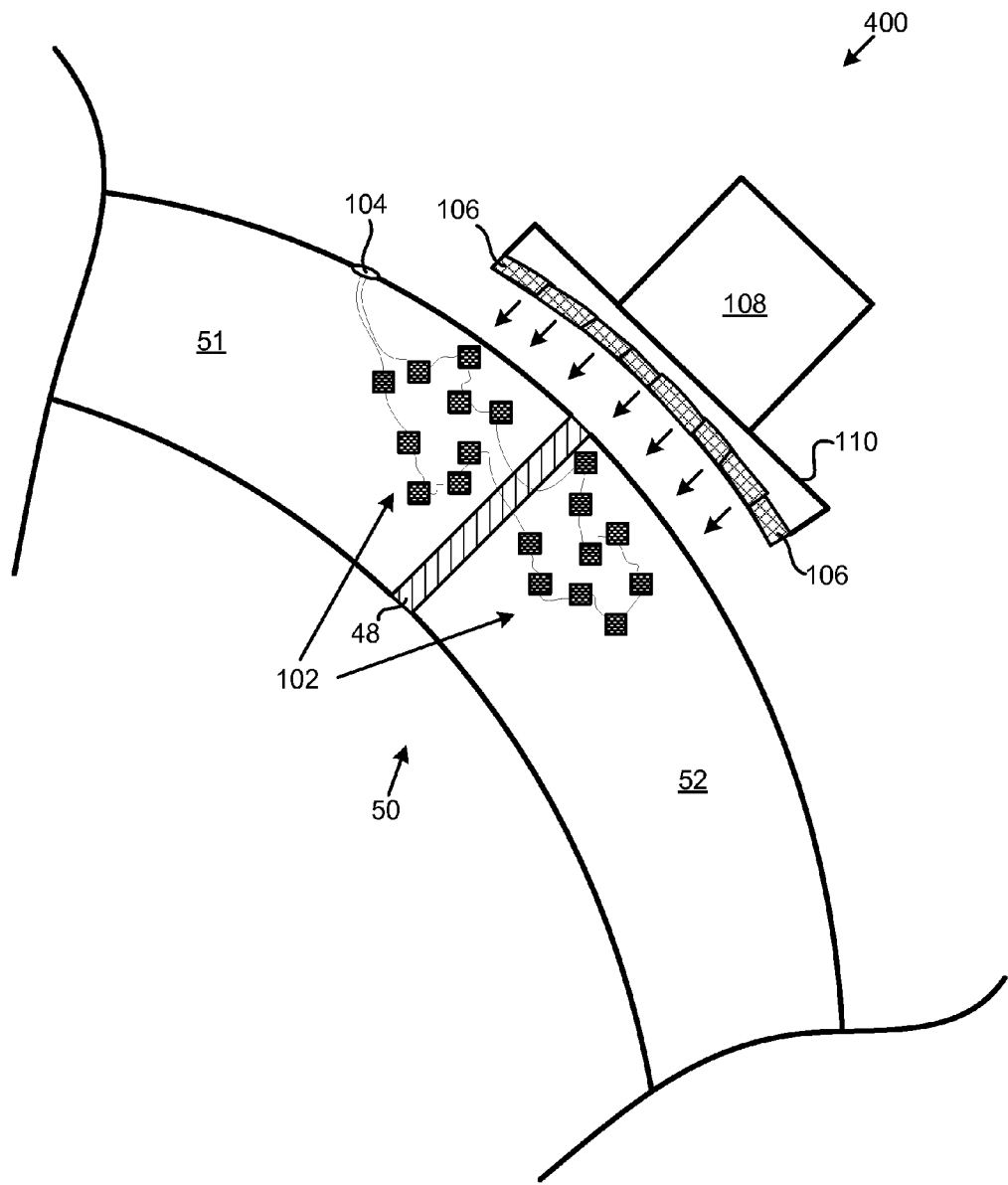
FIG. 4 depicts one embodiment of a system for in situ strength testing of a bonded joint that includes element force energizers, an energy interface, a sensor, and a recording device.

FIG. 4 depicts one embodiment of a system 400 for in situ strength testing of a bonded joint that includes element force energizers 102, an energy interface 104, a sensor 106, a recording device 108, and a patch 110. The recording device 108 may be a mechanism that records and stores the data detected by the sensors 106. In another embodiment, the recording device 108 may also function as a transmitter and may have a configuration that allows it to communicate the data from the sensors 106 to a controller (see, e.g., FIG. 5 for one specific embodiment of a controller). For example, the recording device 108 may communicate the data to a main systems controller of a product or to a product servicing and repair agency. In other words, the recording device 108 may communicate the conditions of the bonded joint to an electronics control module for further processing. Additionally, in one embodiment the recording device may not actually be a separate component and may be integrated with the sensors 106. FIG. 4 also depicts a patch 110 removed a distance away from the bonded joint 50. In such an implementation, as discussed above, the patch 110 may be detachable and thus it may be repeatedly removed from the bonded joint 50 during operation of the structure and reattached to the bonded joint 50 during testing. However, FIG. 4 may also represent a manufacturing step in which the patch 110 is about to be permanently bonded to the existing bonded joint 50.

Figure 5:
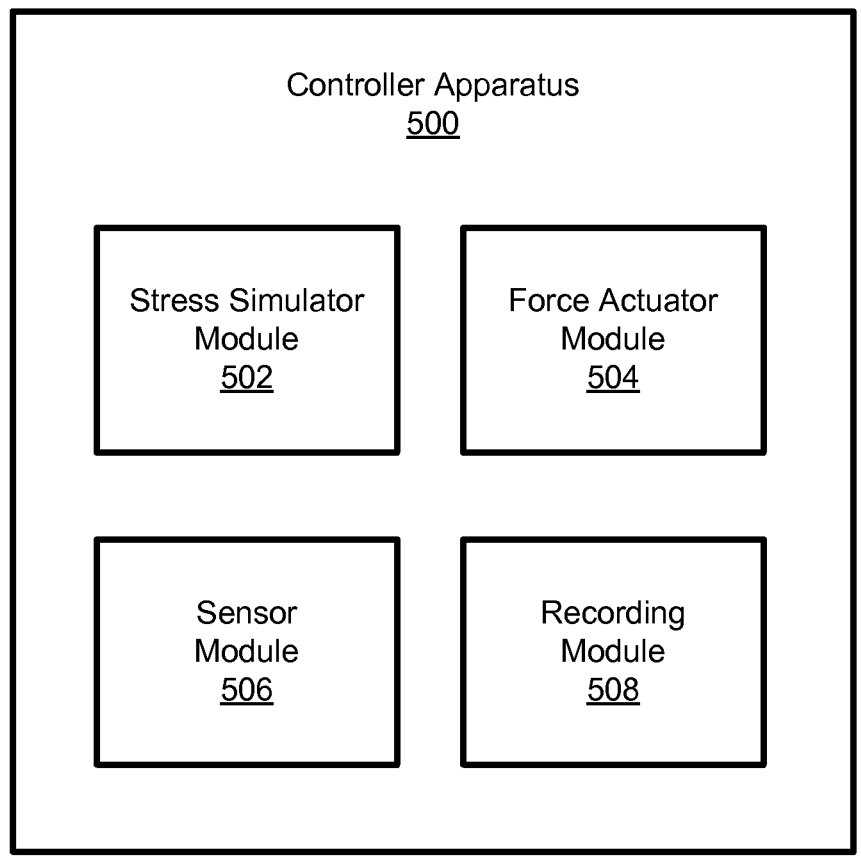
FIG. 5 is a schematic block diagram of one embodiment of a controller apparatus for controlling in situ strength testing of a bonded joint that includes a stress simulator module, an element force energizer module, a sensor module, and a recording module.

FIG. 5 is a schematic block diagram of one embodiment of a controller apparatus 500 for controlling in situ strength testing of a bonded joint that includes a stress simulator module 502, an element force energizer module 504, a sensor module 506, and a recording module 508. The stress simulator module 502 may be configured to generate a predetermined mechanical fatigue profile that includes desired mechanical stress commands. The desired mechanical stress commands may represent requested or expected implementation load spectrums. In other words, as briefly described above, the mechanical fatigue profile for an airframe of an aircraft, for example, may include expected mechanical stress data related to the expected or standard mechanical stress experienced by an aircraft over the course of its useful life. Thus, according to one embodiment, the stress simulator module 502 may be configured to generate a mechanical fatigue profile that represents a lifetime of load-bearing use. In another embodiment, however, the stress simulator module 502 may generate a mechanical fatigue profile that represents a maximum load. In other words, the mechanical fatigue profile at least represents a set of testing procedures or commands to be executed by the element force energizers 102 (and other regulators/actuators) in order to test a certain aspect of the bonded joint 50.

The controller apparatus 500 also includes an element force energizer module 504. The element force energizer module 504 receives the mechanical fatigue profile from the stress simulator module 502 and sends corresponding actuator commands to the element force energizers 102 coupled to the components 51, 52 or the bonded joint 50 and/or to the energy interface 104. Thus, the element force energizer module 504 controls the frequency, intensity, magnitude, and scale of the force imparted to the bonded joint (based on the mechanical fatigue profile) by regulating the power delivered to the actuators 102 via the energy interface 104 or through various other regulators, according to one embodiment.

The sensor module 506 and the recording module 508 are configured to receive the data measured from the sensors 106 relating to the actual stress and strain of the bonded joint. In one embodiment, the sensor module 506 may receive the strain data detected by the sensors 106 and may pass along a mechanical stress report to the recording module 508. The recording module 508 may be configured to store the data, transmit the data to another control system, or otherwise analyze the mechanical stress report data. According to one embodiment, the recording module 508 may compare the data to the mechanical fatigue profile generated by the stress simulator module 502. Depending on the detected strain or stress in the bonded joint 50, the recording module 508 may thus resolve the strength rating of the bonded joint and may determine whether the bonded joint 50 is sufficiently mechanically sound to be used for its intended purpose.

Figure 6:
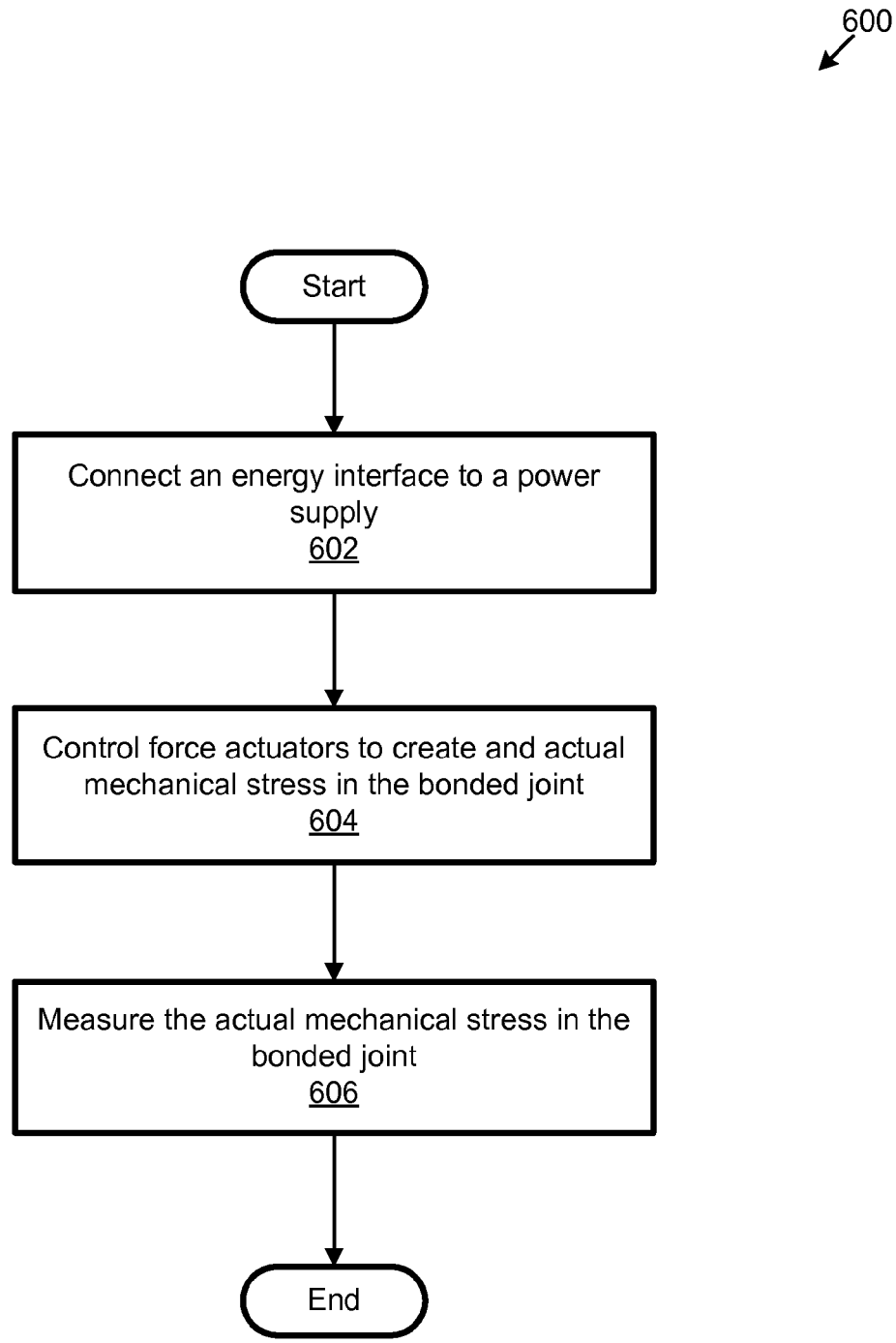
FIG. 6 is a schematic flowchart diagram of one embodiment of a method for in situ strength testing of a bonded joint.

FIG. 6 schematic flowchart diagram of one embodiment of a method 600 for in situ strength testing of a bonded joint 50. The method 600 includes connecting 602 an energy interface to a power supply, controlling 604 element force energizers to create an actual mechanical stress in the bonded joint 50, and measuring 606 the actual mechanical stress in the bonded joint 50. Connecting 602 an energy interface to a power supply may include supplying power to the energy interface. In a further embodiment, the method may include recording the actual mechanical stress measured in the bonded joint 50. As described above, the method may also include comparing the measured mechanical stress in the bonded joint with the mechanical fatigue profile (i.e., the expected mechanical stress). If the actual measured mechanical stress is different than from what was expected, it may be concluded that the bonded joint 50 has potentially suffered a defect or is structurally compromised to a certain degree, according to one embodiment.

In one embodiment, the system may not be active while the structure of the bonded joint 50 is in operation and may only be activated during maintenance checks or periods of repair. It is also contemplated that the system, apparatus, and method of the present disclosure may be implemented in other various configurations and for various other purposes while still falling with the scope of the present disclosure. For example, the sensors 106 may be continually monitoring the stress or strain in the bonded joint 50 and when a certain condition is detected, the controller apparatus 500 may actuate the element force energizers 102 to temporarily increase rigidity to the bonded joint structure or otherwise affect the components 51, 52. Thus, according to one embodiment, the system may be used as a feedback control system.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive.

What is claimed is:

1. A system for testing the strength of a bonded joint between two components, the bonded joint comprising an adhesive interposed between the two components, the system comprising:
   at least one element force energizer that creates an actual mechanical stress in the bonded joint when actuated, wherein the at least one element force energizer is embedded in at least one of the two components;
   an energy interface that is connectable to a power source, the energy interface being in electrical communication with the at least one element force energizer; and
   a sensor that detects the actual mechanical stress in the bonded joint.

2. The system of claim 1, further comprising a recording device in communication with the sensor that receives and records data of the actual mechanical stress from the sensor.

3. The system of claim 1, wherein the at least one element force energizer creates mechanical stress according to a predetermined mechanical fatigue profile.

4. The system of claim 1, wherein the at least one element force energizer is not disposed in the adhesive.

5. The system of claim 1, wherein the at least one element force energizer comprises piezoelectric material.

6. The system of claim 1, wherein the at least one element force energizer comprises load cells.

7. The system of claim 1, wherein the sensor comprises at least one of a piezoelectric sensor and a fiber optic sensor.

8. The system of claim 1, wherein the sensor is embedded in at least one of the two components.

9. The system of claim 1, further comprising a controller comprising:
   a stress simulator module configured to generate a predetermined mechanical fatigue profile, wherein the predetermined mechanical fatigue profile comprises desired mechanical stress commands;

an element force energizer module configured to receive the mechanical fatigue profile and to control the at least one element force energizer to create an actual mechanical stress in the bonded joint according to the mechanical fatigue profile; and a sensor module configured to receive data from the sensor relating to the actual mechanical stress in the bonded joint.

10. The system of claim 9, further comprising a recorder module that receives and records the data from the sensor module.

11. The system of claim 9, wherein the at least one element force energizer is not disposed in the adhesive.

12. The system of claim 9, wherein the element force energizers comprise at least one of piezoelectric materials and hydraulic actuators.

13. A method for testing the strength of a bonded joint between two components, the bonded joint comprising an adhesive interposed between the two components, the method comprising:

supplying power to an energy interface coupled to element force energizers, wherein the element force energizers are embedded in at least one of the two components;

controlling the element force energizers to create an actual mechanical stress in the bonded joint based on the power; and measuring the actual mechanical stress in the bonded joint.

14. The method of claim 13, further comprising recording the actual mechanical stress measured in the bonded joint.

15. The method of claim 13, wherein the element force energizers are not disposed in the adhesive and are embedded in at least one of the two components proximate the adhesive.

16. A system for testing the strength of a bonded joint between two components, the bonded joint comprising an adhesive interposed between the two components, the system comprising:

at least one element force energizer that creates an actual mechanical stress in the bonded joint when actuated, wherein the at least one element force energizer is not disposed in the adhesive;

an energy interface that is connectable to a power source, the energy interface being in electrical communication with the at least one element force energizer; and a sensor that detects the actual mechanical stress in the bonded joint.

* * * * *